United States Patent [19]

Mossholder

[11] Patent Number: Plant 7,416

[45] Date of Patent: Jan. 8, 1991

[54] AZALEA HYBRID 'RACHEL BANDY'

[75] Inventor: Rose M. Mossholder, Fallbrook, Calif.

[73] Assignee: Hines Nurseries Inc., Irvine, Calif.

[21] Appl. No.: 351,492

[22] Filed: May 15, 1989

[51] Int. Cl.[5] ..... A01H 5/00

[52] U.S. Cl. ..... Plt./57

[58] Field of Search ..... Plt./55–57

[56] References Cited

PUBLICATIONS

Leach, D. G. (Listing), 'Rachel' *Rhododendrons of the World,* Charles Scribner's Sons, N.Y., 1961, p. 486.

*Primary Examiner*—James R. Feyrer

*Attorney, Agent, or Firm*—Klarquist, Sparkman, Campbell, Leigh & Whinston

[57] ABSTRACT

The new plant is a hybrid evergreen azalea having a compact, vigorous horizontally spreading form. The azalea has a prolific blooming habit with florist quality blossoms that appear in clusters of two to four. The blooms are very large and semidouble with a diameter of about 10 to 11.4 cm. They have a magenta-rose color with the two upper wing petals dotted and a mildly sweet fragrance.

3 Drawing Sheets

BACKGROUND OF THE INVENTION

The present invention relates to a new and distinct variety of evergreen azalea of the genus Rhododendron and a member of the Ericaceae family. This new variety of azalea plant is the result of a breeding program. The principal objectives of this breeding program were to produce new varieties of evergreen azaleas which are floriferous, compact, vigorous, and easy to propagate using vegetative cuttings.

The specific parentage of the new variety is unknown because no records were kept of the crosses made which resulted in the new plant. The breeding program incorporated the use of forty seven varieties of evergreen azaleas from seven hybrid groups that were grown at Mossholder nurseries in La Habra, Calif.

Hybrid Groups Used in the Breeding Program

| | # of Cultivars |
|---|---|
| Belgian Indian Hybrids | 25 |
| Coolidge Hybrids | 3 |
| Mossholder-Bristow Hybrids | 11 |
| Pericat Hybrids | 2 |
| Rutherford Hybrids | 2 |
| Southern Indian Hybrids | 1 |
| Kurume Hybrids | 3 |

'Rachel Banda' most closely resembles the Belgian Indian Hybrid Group. Of the plants used in the breeding program, 'Orchidflora', 'Rose Queen', and 'Sweetheart Supreme' were most similar to the new selection.

This new hybrid has the following combination of characteristics which distinguish it from other varieties.

1. Flower size, color, form, and fragrance. The hube 10.0 to 11.4 cm blooms are magneta rose, semidouble, and emit a mildly sweet fragrance. Blooms mid-season (early March–April).

2. Plant form and vigor. The plant is horizontally spreading, compact, vigorous and has a prolific blooming habit.

3. Ease of Vegetative Propagation. The new hybrid has been asexually reproduced thousands of times by cuttings at Hines Nurseries in Irvine, Calif. Each of the progeny exhibits characteristics identical to the original mother plant, establishing the hybrid as reproducible and true to type.

DESCRIPTION OF THE PHOTOGRAPHS

DETAILED PLANT DESCRIPTION

The following is a description of the new hybrid azalea plant, Color determinations and comparisons are all based on The Royal Horticultural Society Colour Chart.

Origin: Hybrid seedling.

Parentage: Unknown.

Classification: Hybrid.

Form: Irregular dome shape.

Growth: Compact and vigorous.

Figure 1:
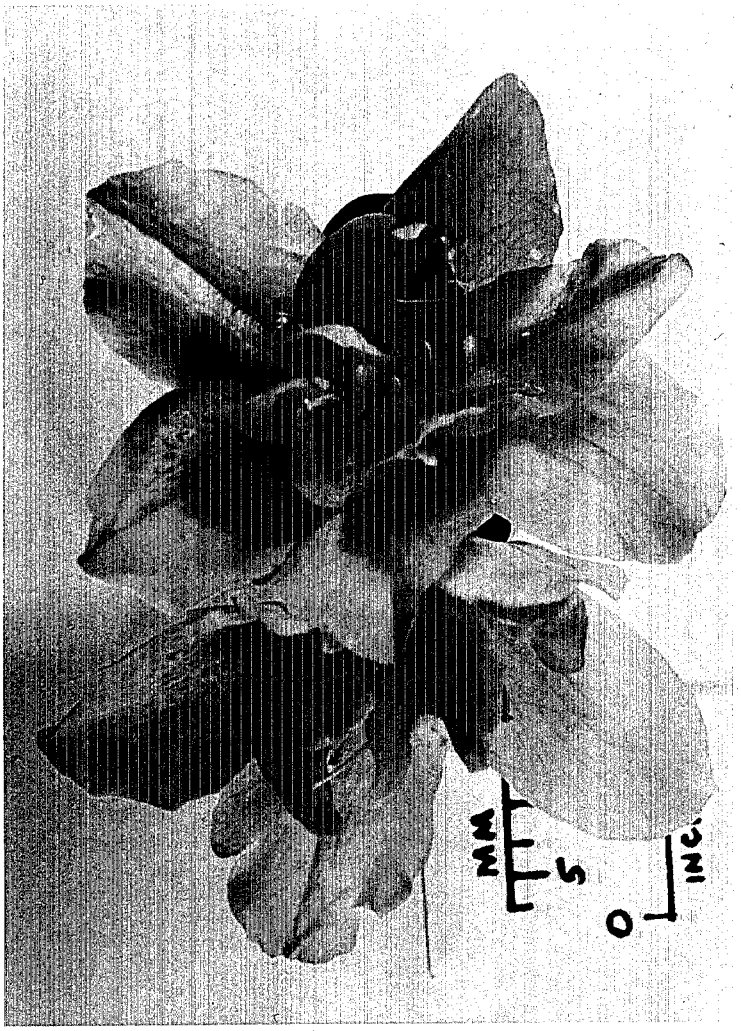
FIG. 1 is a close-up of the flowers demonstrating the size, color, and form.
Figure 2:
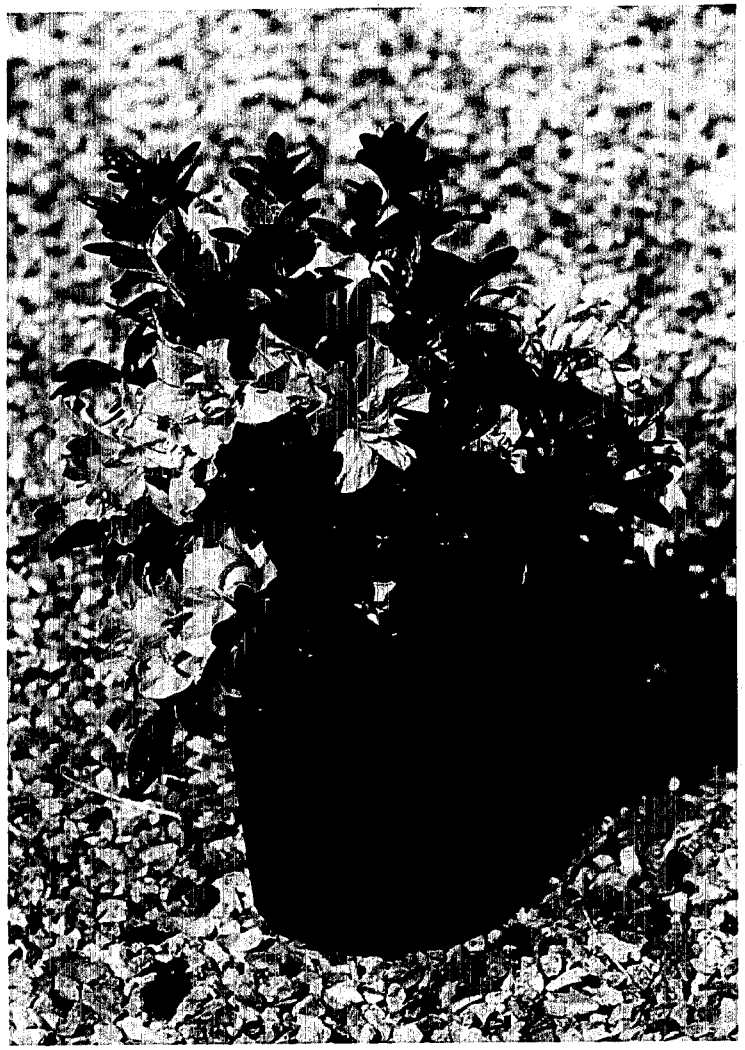
FIG. 2 shows the overall appearance of the compact growth habit and prolific blooming habit.
Figure 3:
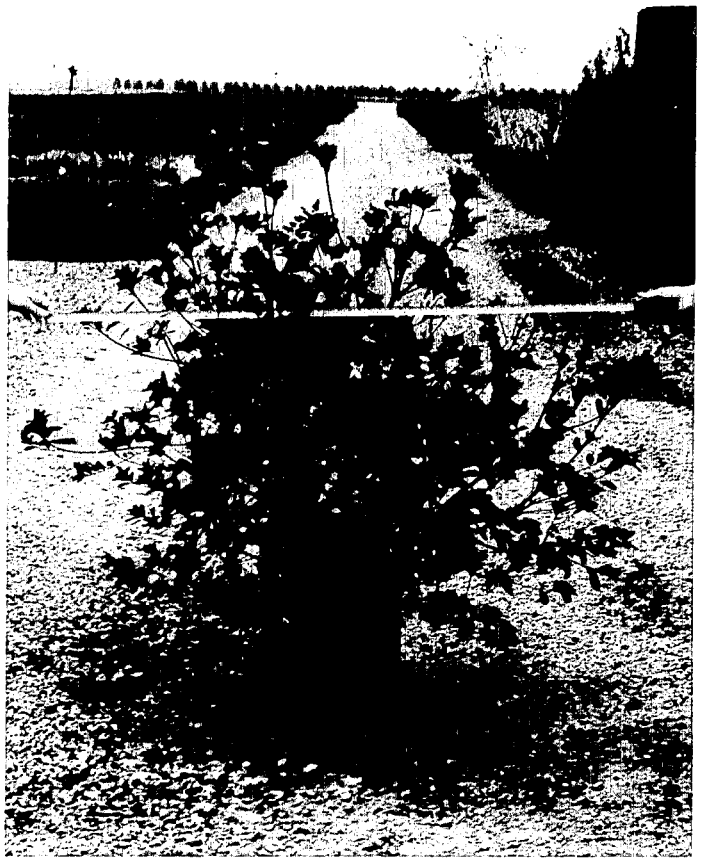
FIG. 3 is a photograph of the nearly mature 9 year old plant in bud.

Size: Height of a 9 year old plant in a #15 container reached 109 cm (43 inches). The branches spread to a width of 145 cm (57 inches). FIG. 3 shows a 9 year old plant with spreading habit. Estimated height for a 10 year old mature plant is about 121 cm (47.5 inches) with a spread of 156 cm (61.5 inches).

Plant vigor: Active, strong growth on the plant's own rootstock (vigorous). Estimated annual terminal growht averages 23 cm.

Habit: Dense and twiggy (compact) in youth. Spreading and ascending branches with maturity. As the plant matures the width becomes greater than the height. Branch positions are whorled.

Blooming habit: Prolific.

Blooming period: Flowers appear in mid-February and blooms continue throug mid-April at Irvine, Calif. Blooms have also appeared during early August through early September.

Disease resistance: Normal as compared with other azalea varieties grown under the same cultural conditions at Irvine, Calif.

HARDINESS

Minimum temperature range for 'Rachel Banda' is normally in the range of −7° C. to −1° C. (20° to 30° F.). Minor frost damage occured to newly formed foliage and flower buds in February at Irvine, Calif. when the temperature dropped to −3° C. (26° F.). The plants have not been tested for maximum cold hardiness.

FOLIAGE

Arrangement: Alternate.

Type: Evergreen.

Shape: Ellitical to obovate, acute to obtuse, cuneate, flat.

Size: Average length of mature foliage (from petiole to leaf apex) is about 7.8 cm. Average width of mature foliage is about 3.2 cm.

Color:

*Upper leaf surface.*—Fan 3, yellow-green group No. 147A.

*Lower surface.*—Fan 3, yellow-green group No. 146A.

Margins: Entire, ciliate.

Texture: Glossy, coarse, strigose. Color of indumentum on young leaves, yellow-white group No. 158A to 164D. Color of indumentum on mature leaves, grey-orange group No. 164A to 166D.

Petiole: Sericeous, coppery brown, yellow-green group No. 145B. Average length 0.8 cm.

Buds: Elliptic, yellow-green group No. 144B, C, covered with copper brown sericeous hairs. As buds open and leaf unfolds hairs are whitish.

Stems:

*Young growth.*—Yellow green group No. 144B to 145A. Sericeous to strigose hairs range from grey-orange group No. 164D to 166C.

*Maturing growth.*—Grey-orange group No. 165B to 166C or D. Strigose, hair color is whitish to coppery brown, grey-orange group No. 164D to 165C.

INFLORESCENSE

Flowers borne: In clusters of two to four.

Petalage: Five lobes fused at base with 5–7 petaloid stamens, connate. Color, Fan 2, red-purple group No. 57B. The standard petal and the two upper wing petals are dotted, Fan 2, red-purple group No. 60B.

Pedicel: Length 1.4 cm, yellow-green group No. 145B with whitish sericeous hairs.

Margin: Slightly undulate.

Fragrance: Mildly sweet scent.

Form: Semidouble, widely funnel shaped with petaloid stamens.

Size: Very large, 10 to 11.4 cm in diameter and 5.5 to 6.0 cm in length.

Persistence: Petals hang and dry, turn various shades of red-purple to brown, discolored with age.

Calyx: Persistent, lanceolate, acute, valvate, yellow-green group No. 145A with sericeous hairs ranging from yellow-white No. 158A to grey-orange No. 164D. Average length about 1 cm.

Flower buds: At an approximate age of two weeks buds were still tight and were elliptic and acute with a length of 4 cm and a diameter of 0.7 cm. The color was not significantly different from mature flowers.

REPRODUCTIVE ORGANS

Stamens: Petaloid stamens, average 5 to 7, variable, with red-purple group No. 57A to 58A anthers depending on maturity. White pollen present but not tested for viability.

Pistils: Single, average length 4.5 cm, equal to or longer than petal length, almost twice as long as stamens. Color of style base is yellow-green group No. 153C ascending to red-purple group No. 58B, C depending on age.

Ovary: Five locules with a hypogynous ovary enclosed by a sericeous ovary wall.

DESCRIPTIONS OF MOST SIMILAR KNOWN AZALEA CULTIVARS

Azalea 'Rachel' Banda has huge 10.0 to 11.4 cm diameter blooms that are magenta rose, semidouble, emit a mildly sweet fragrance, and open in mid-season. The following cultivars represent those known that are most similar to 'Rachel Banda'.

'Orchidflora': Moderate pink, semidouble, blooms mid to late season (March to May).

'Rose Queen': Deep purplish pink, white throat, dark blotch, semidouble, hose-in-hose, 3.3 cm, blooms early mid season (February).

'Sweetheart Supreme': Deep pink, blotch darker, hose-in-hose, semidouble, frilled, 4.6 cm, Late season bloomer (April–May).

REFERENCES

Galle, F., *Azaleas,* Revised and Enlarged Edition, Timber Press, Portland, Ore. (1987).

Hines Nurseries, 1989 *Nursery Catalog,* Irvine, Calif.

Kofranek, A. and Larson, R., *Growing Azaleas Commercially,* The University of California's Cooperative Extension Program (1975).

Medfeld's Nursery, Inc., 1988–1989 *Nursery Catalog,* Riverside, Calif.

Nuccio's Nurseries, 1988–1989 *Catalog,* Altadena, Calif.

I claim:

1. A new and distinct variety of evergreen azalea as described and illustrated, characterized by a compact, vigorous horizontally spreading form and a prolific blooming habit with flowers that appear in clusters of two to four, very large semidouble blooms with a diameter of about 10 to 11.4 cm, and a magenta-rose color with the two upper wing petals dotted, and a mildly sweet fragrance.

* * * * *

UNITED STATES PATENT AND TRADEMARK OFFICE

CERTIFICATE OF CORRECTION

PATENT NO. : Plant 7,416

DATED : January 8, 1991

INVENTOR(S) : R. M. Mossholder

It is certified that error appears in the above-identified patent and that said Letters Patent is hereby corrected as shown below:

On the title page, item:

[54] Plant patent title, AZALEA HYBRID 'RACHEL BANDY' should be --AZALEA HYBRID 'RACHEL BANDA'--;

Column 1, line 34

"hube" should be --huge--;

Column 2, line 15

"plant, Color" should be --plant. Color--;

Column 2, line 32

"growht" should be --growth--;

Column 2, line 39

2), "throug" should be --through--;

Column 3, line 13

"Ellitical" should be --Elliptical--; and

UNITED STATES PATENT AND TRADEMARK OFFICE

CERTIFICATE OF CORRECTION

PATENT NO. : Plant 7,416

DATED : January 8, 1991

INVENTOR(S) : R.M. Mossholder

It is certified that error appears in the above-identified patent and that said Letters Patent is hereby corrected as shown below:

Column 4, line 24, "'Rachel' Banda" should read --'Rachel Banda'--.

Signed and Sealed this

Seventeenth Day of August, 1993

*Attest:*

*Attesting Officer*

BRUCE LEHMAN

*Commissioner of Patents and Trademarks*